United States Patent [19]

Arcamone et al.

[11] 4,024,224

[45] May 17, 1977

[54] 14-AMINODAUNOMYCINS, THEIR PREPARATION AND USE

[75] Inventors: Federico Arcamone, Nerviano (MI); Luigi Bernardi, Milan; Bianca Patelli, Milan; Aurelio di Marco, Milan, all of Italy

[73] Assignee: Societa' Farmaceutici Italia S.p.A., Milan, Italy

[22] Filed: Dec. 3, 1975

[21] Appl. No.: 637,170

[30] Foreign Application Priority Data

Dec. 24, 1974 United Kingdom ............ 55796/74

[52] U.S. Cl. .................................. 424/180; 536/4; 536/17
[51] Int. Cl.² .................. C07H 15/22; A61K 31/71
[58] Field of Search .... 260/210 R, 210 AB, 211 R; 536/4, 17; 424/180

[56] References Cited

UNITED STATES PATENTS

| | | | |
|---|---|---|---|
| 3,037,015 | 5/1962 | Rudy et al. .................... | 260/211 R |
| 3,133,912 | 5/1964 | Kimmig et al. .............. | 260/211.5 R |
| 3,803,124 | 4/1974 | Arcamone et al. ......... | 260/210 AB |
| 3,957,755 | 5/1976 | Jolles ............................ | 260/210 R |

OTHER PUBLICATIONS

Noller, "Chem. of Organic Compounds," 3rd Ed., W. B. Saunders Co., Phila. Pa., 1965, pp. 252 and 253.

*Primary Examiner*—Johnnie R. Brown
*Attorney, Agent, or Firm*—Hubbell, Cohen, Stiefel & Gross

[57] ABSTRACT

14-Aminodaunomycins, which are prepared by reacting 14-bromodaunomycin with an amine in a solvent at about 20°–60° C. are useful in treating certain tumors such as ascites Sarcoma 180 and solid Sarcoma 180.

12 Claims, No Drawings

14-AMINODAUNOMYCINS, THEIR PREPARATION AND USE

BACKGROUND OF THE INVENTION

1. Field of the Invention

The present invention relates to novel daunomycin derivatives, processes for their preparation and the use thereof.

2. Description of the Prior Art

Daunomycin and Adriamycin are known antitumor glycoside antibiotics respectively described and claimed in British Pat. Nos. 1,033,383 and 1,161,278 and 1,217,133, all of which are owned by the unrecorded assignee hereof. The starting material for the preparation of the novel compounds of this invention, 14-bromodaunomycin, in a known compound and can be obtained according to the procedures described in said British Pat. No. 1,217,133.

SUMMARY OF THE INVENTION

The novel daunomycin derivatives of the invention are the 14-amino derivatives having the general formula I, and pharmaceutically acceptable acid addition salts thereof:

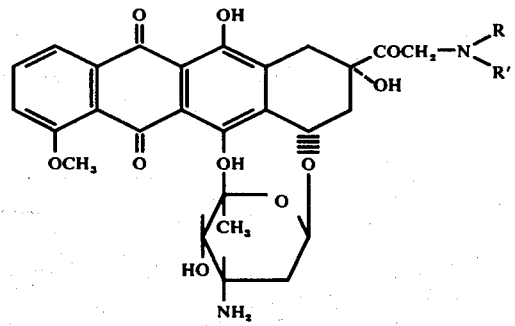

wherein R and R' are independently selected from the group consisting of hydrogen, lower alkyl, hydroxy lower alkyl, dihalo lower alkyl, amino lower alkyl and (lower alkyl amino) lower alkyl, with the proviso that R and R' are not both hydrogen and wherein R and R', together with the nitrogen atom to which they are bound, may form a heterocyclic ring, optionally containing a further hetero atom in addition to the nitrogen atom shown in formula I. Examples of such heterocyclic rings are piperidino, pyrrolidino, morpholino, piperazino, lower alkyl-piperazino, hydroxy lower alkyl-piperazino and halo lower alkyl-piperazino.

As used herein the term "lower alkyl" means straight and branched chain alkyl groups containing up to 4 carbon atoms.

The invention also provides processes for the preparation of the above-described daunomycin derivatives and their acid addition salts. The process comprises reacting 14-bromodaunomycin, which has the general formula II:

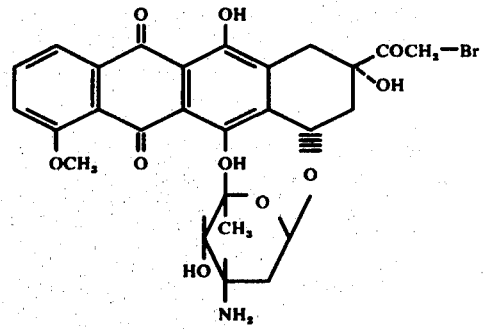

or an acid addition salt thereof, with the appropriate primary or secondary amine of the formula NHRR', wherein R and R' are as defined above in an organic solvent, such as acetone or t-butanol, at a temperature of about 20° C. to 60° C., and, if desired, acidifying the resulting product to obtain the acid addition salt. The novel daunomycin derivatives of the invention are useful in the treatment of certain neoplastic diseases as will be described in more detail below. Their antitumor activity is as effective as that of daunomycin, but they display a much lower toxicity than daunomycin.

BIOLOGICAL ACTIVITY

The biological activity of the compounds of the invention, in terms of both in vitro and in vivo activity, will now be described.

In vitro studies

Mouse embryo fibroblasts (MEF) were plated on 35 mm. Falcon plastic dishes and infected 24 hours later with Moloney Sarcoma Virus (MSV) in the presence of DEAE-dextran (25 $\mu$g./ml.). The samples were then treated for 3 days with different concentrations of the compounds of the invention. The number of foci of transformed cells was microscopically determined 5 days after the infection. Uninfected MEF were similarly treated and at the end of the experiment, the cells were counted in an haemocytometer. In all the experiments, the cells were incubated in a 5% $CO_2$ incubator at 37° C.

For use in these tests the compounds were dissolved in distilled water or in 5% ethyl alcohol in distilled water and then diluted in culture medium.

The results of these tests are reported in Table I in terms of $ID_{50}$ values (Inhibiting Dose 50%), calculated on dose-effects lines.

In vivo studies

The antitumor activity of the compounds of the invention was tested on ascites Sarcoma 180.

Three month old CD 1 mice were used. Sarcoma 180 ascites cells were inoculated intraperitoneally ($10^6$ cells/mouse). For use in these tests, the compounds were dissolved in distilled water or in 5% ethyl alcohol in distilled water, then diluted with Ringers solution and administered i.p. 1 day after the tumor implant (10 ml./kg. of body weight).

The toxicity of the test compounds was evaluated by macroscopic autoptic examination mainly in terms of reduction in spleen size. The comparison of the effectiveness of the test compounds is based on the maximum increase in median survival time, as compared to untreated controls, over the dose range used. The number of Long Term Survivors (LTS) refers to tumor-free mice at the end of the experiment (60 days). The effect observed on ascites Sarcoma 180 is reported in Table II. Solid Sarcoma 180 was implanted subcutaneously by trocar in the flank of CD 1 mice according to standard methods. The mice were treated i.v. for 5 consecutive days, starting 1 day after the tumor implant. On the 11th day the tumor volume was measured by means of a caliper and evaluated according to the formula ($a^2 \times b$)/2, $a$ and $b$ being the minimum and the maximum diameters respectively. The results are reported in Table III.

TABLE I

In Vitro Activity On MSV-M Foci Formation And On MEF*Proliferation

| Compound | Dose (μg/ml.) | MSV-M No. of foci % | MSV-M ID 50 (μg/ml.) | MEF* No. of cells % | MEF* ID 50 (μg/ml.) |
|---|---|---|---|---|---|
| Daunomycin | 0.0250 | 0 | | 22 | |
| | 0.0125 | 17 | 0.006 | 45 | 0.0086 |
| | 0.0062 | 51 | | 55 | |
| Adriamycin | 0.0250 | 0 | | 37 | |
| | 0.0125 | 24 | 0.005 | 42 | 0.01 |
| | 0.0062 | 46 | | 61 | |
| 14-(N-morpholino)-daunomycin | 0.4 | 0 | | 21 | |
| | 0.1 | 17 | 0.032 | 31 | 0.5 |
| | 0.0250 | 69 | | 68 | |
| | 0.0062 | 78 | | 81 | |
| 14-[N-(N'-methyl)-piperazino]-daunomycin | 0.4 | 0 | | 23 | |
| | 0.1 | 19 | 0.011 | 56 | 0.09 |
| | 0.0250 | 35 | | 64 | |
| | 0.0062 | 60 | | 67 | |
| 14-(N-piperidino)-daunomycin | 0.4 | 0 | | 24 | |
| | 0.1 | 42 | 0.08 | 58 | 0.1 |
| | 0.0250 | 89 | | 71 | |
| | 0.0062 | 100 | | 87 | |
| 14-(N-(N'-hydroxyethyl)-piperazino]-daunomycin | 0.4 | 2 | | 31 | |
| | 0.1 | 43 | 0.045 | 52 | 0.08 |
| | 0.0250 | 64 | | 64 | |
| | 0.0062 | 71 | | 67 | |
| 14-diethanol-amino-daunomycin | 0.4 | 0 | | 25 | |
| | 0.1 | 21 | 0.052 | 56 | 0.13 |
| | 0.0250 | 73 | | 95 | |
| | 0.0062 | 75 | | 100 | |

*Mouse Embryo Fibroblasts

TABLE II

Activity On Ascites Sarcoma 180

| Compound | Dose (mg./kg.) | T/C[1] % | LTS[2] | % LTS | Toxic[3] Deaths | % Toxic Deaths |
|---|---|---|---|---|---|---|
| Daunomycin | 0.2 | 106 | 1/20 | 5 | 0/20 | 0 |
| | 1 | 193 | 9/20 | 45 | 0/20 | 0 |
| | 5 | 173 | 3/20 | 15 | 3/20 | 15 |
| Adriamycin | 0.2 | 148 | 5/30 | 16 | 0/30 | 0 |
| | 1 | 177 | 13/29 | 45 | 0/29 | 0 |
| | 5 | 200 | 9/47 | 19 | 5/47 | 10 |
| | 10 | 156 | 0/10 | 0 | 2/10 | 20 |
| 14-(N-morpholino)-daunomycin | 0.2 | 103 | 0/10 | 0 | 0/10 | 0 |
| | 1 | 111 | 0/10 | 0 | 0/10 | 0 |
| | 5 | 133 | 3/10 | 30 | 0/10 | 0 |
| | 25 | 223 | 5/17 | 29 | 0/17 | 0 |
| | 50 | 100 | 0/7 | 0 | 1/7 | 14 |
| | 100 | 50 | 1/7 | 14 | 6/7 | 85 |
| 14-[N-(N'-methyl)-piperazino]-daunomycin | 0.2 | 119 | 0/10 | 0 | 0/10 | 0 |
| | 1 | 103 | 0/10 | 0 | 0/10 | 0 |
| | 5 | 116 | 0/10 | 0 | 0/10 | 0 |
| | 12.5 | 167 | 3/10 | 30 | 1/10 | 10 |
| | 25 | 226 | 3/10 | 30 | 0/10 | 0 |
| | 50 | 130 | 1/10 | 10 | 5/10 | 50 |
| 14-(N-piperidino)-daunomycin | 0.2 | 103 | 0/10 | 0 | 0/10 | 0 |
| | 1 | 100 | 0/10 | 0 | 0/10 | 0 |
| | 5 | 140 | 2/10 | 20 | 0/10 | 0 |
| | 12.5 | 200 | 2/10 | 20 | 0/10 | 0 |
| | 25 | 218 | 2/10 | 20 | 0/10 | 0 |
| | 50 | 144 | 2/10 | 20 | 4/10 | 40 |
| 14-[N-(N'-hydroxyethyl)-piperazino]-daunomycin | 0.2 | 103 | 0/10 | 0 | 0/10 | 0 |
| | 1 | 103 | 0/10 | 0 | 0/10 | 0 |
| | 5 | 103 | 1/10 | 10 | 0/10 | 0 |
| | 12.5 | 152 | 0/10 | 0 | 0/10 | 0 |
| | 25 | 222 | 1/10 | 10 | 0/10 | 0 |
| | 50 | 152 | 0/10 | 0 | 3/10 | 30 |
| 14-diethanolamino daunomycin | 0.2 | 106 | 0/10 | 0 | 0/10 | 0 |
| | 1 | 103 | 0/10 | 0 | 0/10 | 0 |
| | 5 | 124 | 0/10 | 0 | 0/10 | 0 |
| | 12.5 | 181 | 0/10 | 0 | 0/10 | 0 |
| | 25 | 187 | 4/20 | 20 | 0/20 | 0 |
| | 50 | 175 | 4/17 | 23 | 0/17 | 0 |
| | 75 | 170 | 0/10 | 0 | 1/10 | 10 |
| | 100 | 83 | 0/7 | 0 | 3/7 | 42 |
| | 200 | 25 | 0/7 | 0 | 7/7 | 100 |

[1]Median survival time, % over untreated controls
[2]Long Term Survivors after 60 days
[3]Number of mice which died as a result of the toxic effect of the compound

TABLE III

Activity On Solid Sarcoma 180

| Compound | Dose (mg./kg.) | Tumor Volume[1] T/C % | Toxic Deaths |
|---|---|---|---|
| 14-(N-morpholine)-daunomycin | 3 | 77 | 0/10 |
|  | 4 | 64 | 0/10 |
|  | 5 | 69 | 0/10 |
| 14-diethanolamino-daunomycin | 12.5 | 82 | 1/5 |
|  | 25 | 66 | 1/5 |
|  | 50 | 44 | 0/5 |

[1]% T/C tumor weight index at 11th day

RESULTS

The activity of the compounds investigated in comparison with the present compounds confirms the fact that modifications in the acetyl side chain in the 9-position of the saturated ring of daunomycin can lead to noticeable modifications in the biological activity. The 14-aminodaunomycins investigated were found to be less active than daunomycin in in vitro tests, but less toxic than daunomycin and adriamycin in mice, the optimal dose being between 12.5 and 25 mg./kg. (1 single treatment i.p. at day 1 after tumor implant), in comparison with optimal doses of 1 or 5 mg./kg. for daunomycin and adriamycin.

The optimal doses resulted in an increase of the life span of mice infected with ascites Sarcoma 180 of about 100%, after a single treatment. It is important to note that with the present compounds, good antitumor effects can be achieved with doses considerably lower than the $LD_{10}$.

On solid Sarcoma 180, the results reported in Table III, show that 14-diethanolaminodaunomycin exerted a marked inhibition of tumor growth, at non-toxic doses.

All the results therefore, strongly suggest that the introduction of a basic group in the side chain of daunomycin leads to marked increases in the antitumor activity, at the optimal dose, in comparison with daunomycin.

DESCRIPTION OF THE PREFERRED EMBODIMENTS

The invention will now be described in more detail in the following preparative examples. All parts given are by weight unless otherwise indicated.

EXAMPLE 1

14-(N-morpholino)-daunomycin

To a suspension of 2 grams of 14-bromodaunomycin hydrobromide in 70 ml. of acetone, 2 ml. of morpholine were added and the solution was maintained at 50° C. for 2 hours.

After removal of the solvent in vacuo, the residue was taken up in 100 ml. of water which was then extracted with four 100 ml. portions of chloroform. The combined chloroform extracts were evaporated under reduced pressure to form a residue which was then dissolved in 20 ml. of methanol, and one equivalent of 0.1 N methanolic HCl was added. 1.6 g. of 14-(N-morpholino)-daunomycin monohydrochloride were precipitated by the addition of diethyl ether; $E_{1.2} = 1.7$; $E_{1\ cm.}^{1\%} = 190$ at 495 nm.

EXAMPLE 2

14-[N-(N'-methyl)-piperazino]-daunomycin

To a suspension of 4 grams of 14-bromodaunomycin hydrobromide in 200 ml. of acetone, 4 ml. of N-methyl-piperazine were added and the solution was maintained at 50° C. for 4 hours.

After removal of the solvent in vacuo, the residue was taken up in 100 ml. of water and extracted with four 100 ml. portions of chloroform. The combined chloroform extracts were then evaporated under reduced pressure to give a residue which was dissolved in 20 ml. of methanol. To the resulting solution was added one equivalent of 0.1 N methanolic HCl. Diethyl ether was then added to precipitate 3 grams of crude 14-[N-(N'-methyl)piperazino]-daunomycin which were then dissolved in 100 ml. of water. The pH of the solution was adjusted to 7 with sodium bicarbonate and the solution was extracted with chloroform.

To the aqueous phase, NaHCO₃ was again added until the pH reached 8.2, and then the solution was repeatedly extracted with chloroform.

The combined chloroform extracts were evaporated off under reduced pressure to yield a residue which was dissolved in 10 ml. of methanol. To the methanol solution was added one equivalent of 0.1 N methanolic HCl. 2.0 g. of 14-[N-(N'-methyl)-piperazino]-daunomycin hydrochloride were precipitated with diethyl ether; $E_{1.2} = 2$; $E_{1\ cm.}^{1\%} = 182$ at 495 nm.

EXAMPLE 3

14-(N-piperidino)-daunomycin

By following the procedures described in Example 1, but using an equivalent amount of piperidine instead of morpholine, 14-(N-piperidino)-daunomycin monohydrochloride was obtained; $E_{1.2} = 1.7$; $E_{1\ cm.}^{1\%} = 192$ at 495 nm. (yield = 65%).

EXAMPLE 4

14-(N-pyrrolidino)-daunomycin

By following the procedures described in Example 1, but using an equivalent amount of pyrrolidine instead of morpholine, 14-(N-pyrrolidino)-daunomycin monohydrochloride was obtained; $E_{1.2} = 1.72$; $E_{1\ cm.}^{1\%} = 202$ at 495 nm. (yield = 66%).

EXAMPLE 5

14-diethylaminodaunomycin

By following the procedures described in Example 1, but using; an equivalent amount of diethylamine instead of morpholine, 14-diethylaminodaunomycin monohydrochloride was obtained; $E_{1.2} = 1.72$; $E_{1\ cm.}^{1\%} = 205$ at 495 nm. (yield = 63%).

EXAMPLE 6

14-bis-chloroethylaminodaunomycin

By following the procedures described in Example 1, but using an equivalent amount of bis-chloroethylamine instead of morpholine, 14-bis-chloroethylaminodaunomycin monohydrochloride was obtained; $E_{1.2} = 1.69$, $E_{1\ cm.}^{1\%} = 180$ at 495 nm. (yield = 68%).

EXAMPLE 7

14-[N-(N'-hydroxyethyl)piperazino]-daunomycin

By following the procedures described in Example 2, but using an equivalent amount of N-hydroxyethyl-piperazine as the amine, 14-[N-(N'-hydroxyethyl)-piperazino]-daunomycin monohydrochloride was obtained; $E_{1,2} = 1.98$; $E_{1\ cm.}^{1\%} = 178$ at 495 nm. (yield = 53%).

EXAMPLE 8

14-diethanolaminodaunomycin

By following the procedures described in Example 2, but using an equivalent amount of diethanolamine instead of N-methyl-piperazine, 14-diethanolaminodaunomycin monohydrochloride was obtained; $E_{1,2} = 1.7$; $E_{1\ cm.}^{1\%} = 188$ at 495 nm. (yield = 42%).

EXAMPLE 9

14-($\beta$-diethylamino)-ethylamino-daunomycin

By following the procedures described in Example 2, but using an equivalent amount of $\beta$-diethylaminoethylamine instead of the N-methyl-piperazine, 14-($\beta$-diethylamino)ethylamino-daunomycin monohydrochloride was obtained; $E_{1,2} = 2.0$; $E_{1\ cm.}^{1\%} = 180$ at 495 nm. (yield = 45%).

Other compounds of the general formula I can also be conveniently prepared by following the above-described techniques and substituting the appropriate amine.

Variations and modifications can, of course, be made without departing from the spirit and scope of the invention.

Having thus described our invention what we desire to secure by Letters Patent and hereby claim is:

1. A daunomycin derivative of the formula:

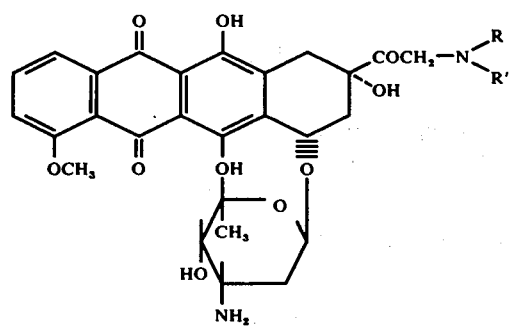

wherein R and R' are independently selected from the group consisting of hydrogen, lower alkyl, hydroxy lower alkyl, dichloro lower alkyl, amino lower alkyl and (lower alkyl amino)-lower alkyl, with the proviso that R and R' are not both hydrogen, and wherein R and R' together with the nitrogen atom to which they are bound may form a heterocyclic ring selected from the group consisting of piperidine, pyrrolidine, morpholine, piperazine, lower alkylpiperazine, hydroxy lower alkylpiperazine and halo lower alkylpiperazine and the hydrochlorides thereof.

2. A compound according to claim 1, which is 14-(N-morpholino)-daunomycin.

3. A compound according to claim 1, which is 14-[N-(N'-methyl)piperazino]-daunomycin.

4. A compound according to claim 1, which is 14-(N-piperidino)-daunomycin.

5. A compound according to claim 1, which is 14-(N-pyrrolidino)-daunomycin.

6. A compound according to claim 1, which is 14-diethylaminodaunomycin.

7. A compound according to claim 1, which is 14-bis-chloro-ethylaminodaunomycin.

8. A compound according to claim 1, which is 14-[N-(N'-hydroxyethyl)piperazino]-daunomycin.

9. A compound according to claim 1, which is 14-diethanolaminodaunomycin.

10. A compound according to claim 1, which is 14-($\beta$-diethylamino)-ethylamino-daunomycin.

11. A method of inhibiting the growth of a tumor selected from the group consisting of ascites Sarcoma 180, and solid Sarcoma 180, said method comprising intraperitoneally or intravenously administering to a host afflicted with said tumor an amount of a compound according to claim 1 sufficient to inhibit the growth of said tumor.

12. A method according to claim 11, wherein the amount of said compound is between 12.5 and 25 mg./kg. of body weight.

* * * * *

UNITED STATES PATENT OFFICE
CERTIFICATE OF CORRECTION

Patent No. 4,024,224   Dated May 17, 1977

Inventor(s) Federico Arcamone et al

It is certified that error appears in the above-identified patent and that said Letters Patent are hereby corrected as shown below:

Column 1, formula I, and column 7, formula I: In both instances, the formula:

" 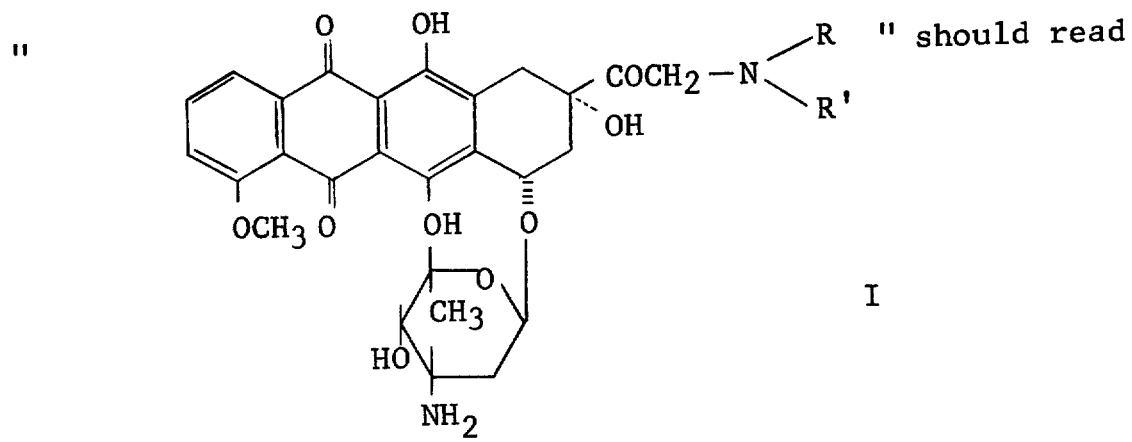 " should read

-- 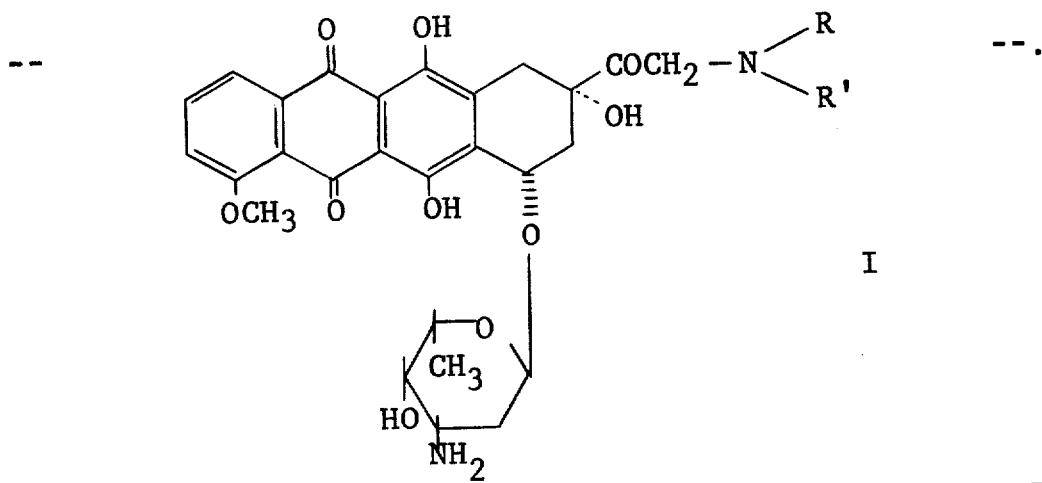 --.

UNITED STATES PATENT OFFICE
CERTIFICATE OF CORRECTION

Patent No. 4,024,224   Dated May 17, 1977

Inventor(s) Federico Arcamone et al

It is certified that error appears in the above-identified patent and that said Letters Patent are hereby corrected as shown below:

Column 1, formula II: The formula:

"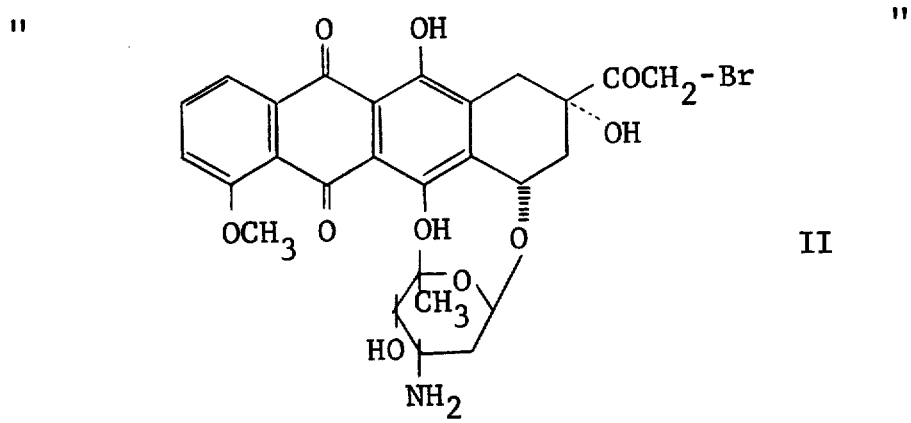"      II should read:

UNITED STATES PATENT OFFICE
CERTIFICATE OF CORRECTION

Patent No. 4,024,224           Dated May 17, 1977

Inventor(s) Federico Arcamone et al

It is certified that error appears in the above-identified patent and that said Letters Patent are hereby corrected as shown below:

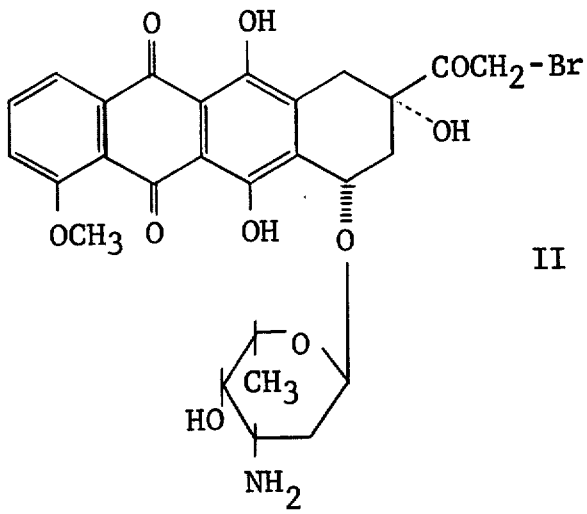

II

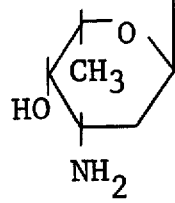

Signed and Sealed this

Eighth Day of November 1977

[SEAL]

Attest:

RUTH C. MASON
Attesting Officer

LUTRELLE F. PARKER
Acting Commissioner of Patents and Trademarks